United States Patent [19]
Bayley et al.

[11] Patent Number: 5,817,771
[45] Date of Patent: Oct. 6, 1998

[54] CELL-TARGETED LYTIC PORE-FORMING AGENTS

[75] Inventors: Hagen Bayley, Grafton; Barbara J. Walker, Auburn, both of Mass.

[73] Assignee: Worcester Foundation for Experimental Biology, Shrewsbury, Mass.

[21] Appl. No.: 364,429

[22] Filed: Dec. 27, 1994

Related U.S. Application Data

[63] Continuation of Ser. No. 54,898, Apr. 28, 1993, abandoned.

[51] Int. Cl.$^6$ .................................................... C07K 9/00
[52] U.S. Cl. ................................... 530/391.7; 530/387.3; 435/183; 435/220
[58] Field of Search ............................ 530/387.3, 391.7; 435/183, 220

[56] References Cited

U.S. PATENT DOCUMENTS

| | | | |
|---|---|---|---|
| 4,867,973 | 9/1989 | Goers et al. | 424/85.91 |
| 4,975,278 | 12/1990 | Senter et al. | 424/94.3 |

OTHER PUBLICATIONS

Bayley, H., "Novel Biomaterials: Genetically Engineered Pores", 1990, *Dept. of Energy Grant No. DE-FG02-90R20018, Worcester Found. for Exptl. Biol.*.
Walker et al., 1994, Protein Eng.,7:91.
Amato, Science, 1992, Feb. 7, 1992, 255:684.
Tobkes et al., Biochem., 24:1915, 1985, Secondary . . . Protein.
Hird et al., Cancer & Genes, 1990, pp. 183–189, Immunotherapy . . . Antobodies.
Osband et al., Immunol. Today, 1:193, 1990, Problems . . . immunotherapy.
Harris, et al.,Tibled, 11:42, 1993, Therapeutic . . . Age.
Thelesstam et al., Toxicon, 26:51; 1998, Staphylococcal . . . Advances.
Pastan et al., Cell, 47:671, 1986, Immunotoxins.
Chounick et al., Cancer. Res., 51:465, 1991, A Recombinant . . . Immunotoxin.
Gray et al., Inf. Immun., 1984, Primary . . . Wood 46, 46:615.

*Primary Examiner*—Frank C. Eisenschenk
*Attorney, Agent, or Firm*—Fish & Richardson P.C.

[57] ABSTRACT

A chimeric compound that contains a cell-specific ligand linked to a pore-forming agent capable of lysing a cell.

4 Claims, 10 Drawing Sheets

LIBRARY OF αHL MUTANTS

- based on a semi-random cassette encoding potential protease-activation site inactive Scre

CELL-TARGETED LYTIC PORE-FORMING AGENTS

This is a continuation of application Ser. No. 08/054,898, filed Apr. 28, 1993, now abandoned.

STATEMENT AS TO FEDERALLY SPONSORED RESEARCH

This invention was made with Government support under DE-FG02-90ER20018 awarded by the Department of Energy, co-sponsored by the Division of Energy Biosciences and the Division of Materials Sciences. The Government has certain rights in the invention.

FIELD OF THE INVENTION

This invention relates to pore-forming compounds.

BACKGROUND OF THE INVENTION

Transmembrane channels or pores can be formed by certain bacterial exotoxins (Bhakdi et al., Philos. Trans. R. Soc. Lond. B. Biol. Sci. 306:311–324, 1983). Pore-forming toxins, such as staphylococcal α-toxin (αHL), assemble into supramolecular amphiphilic polymers in the lipid bilayer of the cell membrane, thus generating stable transmembrane pores.

αHL, a single polypeptide chain of 33,200 daltons, is a water-soluble toxin secreted by *Staphylococcus aureus* (Gray et al., Infect. Immun. 46:615, 1984). αHL is capable of lysing erythrocytes in vitro by forming hexameric structures in the membranes of these cells.

SUMMARY OF THE INVENTION

Despite developments in surgery, radiation therapy and chemotherapy, safe and effective treatments for many cancers has been elusive. Particularly recalcitrant to treatment are metastatic cells that remain after surgery or radiation therapy. These cells are often resistant to conventional chemotherapy.

The invention addresses this problem by providing a pore-forming compound which is active at the surface of the target cell. Limited pore formation can result in permeabilization of the cell membrane which can improve uptake of substances which are normally difficult to deliver into the cytoplasm of cells, such as cytotoxic chemotherapeutic agents or nucleic acids. Extensive pore formation can itself result in the destruction of the cell.

The invention features a chimeric compound composed of two components, each of which has a distinct function. One part of the chimera is a delivery agent which can be a cell-specific ligand capable of specifically binding to a molecule or structure on the surface of a target cell. This ligand is linked to an pore-forming agent which is capable of forming one or more pores in the lipid bilayer of a cell membrane which results in lysis of the cell.

The cell-specific ligand of the chimera, which can be synthetic or natural, may bind to a specific molecule or structure on the surface of a target cell, such as an antigen, growth factor receptor, or viral protein expressed on the surface of an infected cell. Preferably the ligand is an antibody. For therapeutic purposes, the cell-specific ligand or antibody can be one which binds to an unwanted cell in the body, such as a cell which is associated with a pathological condition. Such cells include but are not limited to tumor cells, cells which are chronically infected with virus, or cells, which when improperly regulated or expressed, result in a disease state, e.g., cells of the immune system. Unwanted cells may also be cells which express a recombinant therapeutic nucleic acid as a result of gene therapy. Elimination of such unwanted cells can be a means of regulating or stopping gene therapy.

Preferably, the pore-forming agent, which is capable of forming one or more lytic pores in a target cell, is a bacterial exotoxin, including but not limited to αHL, aerolysin, perfringolysin, pneumolysin, streptolysin O, listeriolysin, *Bacillus thuringensis* toxin, or an *E. coli* -derived lytic molecules such as hemolysin or colicin, or an agent derived from a eucaryotic cell, such as a defensin, magainin, mellitin, complement, perforin, yeast killer toxin or histolysin.

The two components of the chimeric compound are linked via a non-covalent or covalent bond, or both. Preferably the linkage is a covalent bond involving a sulfur atom, more preferably a disulfide, thioester or thioether bond. The compound of the invention can also be produced as a recombinant fusion protein with the two components of the chimera linked by a peptide bond.

The invention also features a mutant pore-forming agent that is inactive, but able to be converted to an active lytic form by conditions or substances at the surface of a target cell as well as a chimeric compound comprising such an activatable agent linked to a cell-specific ligand. Such a molecule may be activated physically, chemically or biochemically. Physical conditions capable of activating the compound of the invention include but are not limited to the presence of heat or light. Chemical conditions capable of activating the pore-forming agent include a change in pH, reduction potential or concentration of metal ions. Biochemical substances, specifically associated with the target cell and capable of activating the compound, include but are not limited to proteases, esterases, glycosidases, ectokinases, or phosphatases. These substances or conditions at the cell surface may be endogenous, e.g., secreted by the target cell, such as a tumor protease, or exogenous, e.g. provided by a source other than the target cell, such as a light emitted from a lamp or fiber-optic device. For example, a therapeutic treatment can comprise topical application of a compound or agent of the invention to a skin tumor and activation by exposure to a light source.

The compound of the invention can be used to treat animals, preferably humans, to destroy unwanted cells associated with a pathological condition. Both the activatable pore-forming agent alone and the chimeric compound of the invention can be administered in a pharmaceutically acceptable carrier for therapeutic use. Unwanted cells, in an animal or removed from an animal, can be destroyed by contacting the target cells with the compound of the invention either alone or together with a chemotherapeutic agent. The compound of the invention and a chemotherapeutic agent may be administered simultaneously or sequentially. A chemotherapeutic agent is defined as a compound or nucleic acid which is cytotoxic to a cell, such as mechloroethamine, cyclophosphamide, ifosfamide, L-sarcolysin, chlorambucil, hexamethylmelamine, thiotepa, busulfan, carmustine, lomustine, semustine, streptozocin, dacarbazine, methotrexate, fluorouracil, cytarabine, mercaptopurine, thioguanine, pentostatin, vinblastine, vincristine, etoposide, teniposide, actinomycin D, daunomycin, doxorubicin, bleomycin, plicamycin, mitomycin, cisplatin, mitoxantrone, hydroxyurea, procarbozine, mitotane, aminoglutethimide, prednisone, hydroxyprogesterone, diethylstilbestrol, tamoxifen, flutamide, or leuprolide, as well as a DNA oligonucleotide, which is complementary to an essential gene of a cell and capable of eliminating or down-regulating expression of such a gene, and a ribozyme which can disrupt protein synthesis of a cell.

The invention also features a method of screening pore-forming compounds for the ability to be activated by a condition or substance associated with a target cell. The candidate compound can be generated by combinatorial mutagenesis of a site involved in interaction with a cell-specific condition or substance. Preferably, target cells are contacted with a candidate compound in the presence and absence of a cell-specific condition or substance and cytolysis evaluated as an indication that the candidate compound is activatable.

DETAILED DESCRIPTION

The drawings are first briefly described.

DRAWINGS

FIGS. 1a–1c are a set of graphs showing activation of hemolytic activity in overlap mutants of αHL by protease treatment. A key to structures of two-chain αHL complementation mutants produced by coupled in vitro transcription/translation (IVTT) is shown in the left panel. The center and right panels show the results of a microtiter assay using two-fold serial dilutions. Assays of mutants which have not been treated with protease are shown in the center graph and assays of replicate samples after treatment with endoproteinase Lys-C (endo C) are shown in the right graph. In each window, the tops of the bars indicate the well with 50% hemolysis after 1 h, 3 h and 24 h (left to right). The top of each window represents well 12 and the bottom well "0" ("0" denotes no hemolysis in well 1). The vertical scale is logarithmic to the base 2. Overlap mutants were activated by adding endo C (1.0 μg) to the IVTT mix (10 μL). The initial dilution of the IVTT mix in well 1 was 1:4. The individual polypeptides that make up the two-chain mutants have no hemolytic activity.

FIG. 2 is a set of graphs showing hemolysis by selected mutants as determined by a spectrophotometric assay. The decrease in light scattered at 600 nm, an indication of erythrocyte lysis, was monitored after the addition of IVTT mix (10 μL, before additions) to 0.025% rabbit erythrocytes (500 μL). The mutants used are as in FIGS. 1a–1c, with the addition of the non-activatable gap mutant αHL(1–131)●(143–293) as a control (bottom left panel).

FIGS. 3a–3b are photographs of endo-C-treated proteolytic fragments of overlap mutants and their component polypeptides separated using sodium dodecylsulfatepolyacrylamide gel electrophoresis (SDS-PAGE).

FIGS. 4a–4b are photographs of an SDS-PAGE gel showing the results of treatment of the two-chain mutants with endo C.

FIG. 7a is a diagram and FIGS. 7b–7c are graphs showing selective proteolytic activation of αHL 1–172●132–293 overlap mutants containing Lys-131 or Arg-131. Rabbit erythrocyte hemolysis was monitored by the decrease in light scattering at 600 nm after the addition of IVTT mix to a suspension of rabbit erythrocytes.

COMPOUNDS OF THE INVENTION

As described in the Summary above, the compound of the invention employs several components which will now be discussed in greater detail.

One component of the compound of the invention is a lytic pore-forming agent, which can be naturally-occurring or synthetically-made. The pore-forming agent can be a molecule as well as a fragment, derivative or analog of such a molecule, which is capable of generating one or more transmembrane pores in the lipid bilayer of a cell which results in the lysis of said cell. Such pore-forming agents derived from bacteria include αHL, *E. coli* hemolysin, *E. coli* colicin, *B. thuringenis* toxin, aerolysin, perfringolysin, pneumolysin, streptolysin O, and listeriolysin. Eucaryotic pore-forming agents capable of lysing cells include defensin, magainin, mellitin, complement, perforin, yeast killer toxin and histolysin. Synthetic organic molecules, such as Pederson's crown ethers and valinomycin, which are capable of forming a lytic pore in a cell membrane can also be used. Other synthetic lytic pore-forming agents are described in Regen et al., Biochem. Biophys. Res. Commun. 159: 566–571, 1989, herein incorporated by reference.

The compound of the invention can also include fragments of naturally-occurring or synthetic pore-forming agents which exhibit lytic activity. In addition to substantially full-length polypeptides, the present invention provides for biologically active fragments of the polypeptides. A pore-forming polypeptide or fragment is biologically active if it is capable of forming one or more lytic pores in natural or synthetically-made lipid bilayers.

Also within the invention is an inactive pore-forming agent of the invention which is incapable of forming pores in natural or synthetically-made lipid bilayers until a substance or condition at the surface of the target cell acts upon it to convert it into an active lytic form. The invention encompasses the mutant inactive pore-forming agent alone as well as linked to a cell-specific ligand.

Biologically active fragments of lytic pore-forming agents can be generated by methods known to those skilled in the art, e.g., proteolytic cleavage or expression of recombinant peptides. The ability of a candidate fragment to permeabilize cell membranes can be assessed by methods known to those skilled in the art, e.g., by the release of intracellular contents, such as ATP or radioactive label from pre-loaded cells or by the uptake of a dye, such as trypan blue which is excluded by intact cells.

As used herein, the term "fragment or segment", as applied to a polypeptide, is at least 5 contiguous amino acids. In the invention, fragments are typically at least 10 contiguous amino acids, more typically at least 20 contiguous amino acids, usually at least 30 contiguous amino acids, preferably at least 40 contiguous amino acids, more preferably at least 50 contiguous amino acids, and most preferably at least 60 to 80 or more contiguous amino acids in length.

The present invention also provides for analogs of naturally-occurring pore-forming agents which can lyse cells. Analogs can differ from naturally-occurring pore-forming agents by amino acid sequence differences or by modifications which do not affect sequence, or by both.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps, e.g., by exposing the polypeptide to enzymes which affect glycosylation e.g., mammalian glycosylating or deglycosylating enzymes. Also included are peptides which have phosphorylated amino acid residues, e.g., phosphotyrosine, phosphoserine, or phosphothreonine or have been modified to add fatty acids.

The invention also includes analogs in which one or more peptide bonds have been replaced with an alternative type of covalent bond (a "peptide mimetic") which is not susceptible to cleavage by peptidases. Where proteolytic degradation of the peptides following injection into the subject is a problem, replacement of a particularly sensitive peptide bond with a noncleavable peptide mimetic can result in a more stable peptide and thus, in most cases, a more useful therapeutic agent. Such mimetics, and methods of incorporating them into polypeptides, are well known in the art. Similarly, the replacement of an L-amino acid residues is a standard way of rendering the polypeptide less sensitive to proteolysis. Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl. Although most modifications are designed to make proteins more resistant to proteolytic degradation, the invention also embraces modifications which enhance such degradation, for the purpose of rapidly eliminating free compound which is not bound to a target cell, thus minimizing therapeutic complications.

Since antibodies to bacterial toxins may exist in patients as a result of previous immunization, infection or treatment with toxin-based therapeutic agents, modifications to render the compound non-immunogenic e.g., by coupling to monomethoxy-polyethylene glycol (mPEG) (Sehon et al., Int. Arch. of Allergy and Immunol. 94:11–20, 1991) are also included.

The invention also includes modifications which result in an inactive pore-forming agent which can be specifically activated by a cell-associated substance or condition. Such a modification can be the addition of a peptide containing an enzymatic cleavage site, e.g., lysine or arginine residues, the peptide bonds of which are hydrolyzed by the enzyme, trypsin. Other modifications, such as the addition of a chemically-reactive group or photoactivated group are also included in the invention. Also, addition of a metal binding site e.g., by the addition of histidine, cysteine or unnatural amino acids, such as 1,2,3 triazole-3-alanine and 2-methyl histidine, which have altered $pK_a$ values, steric properties, and arrangement of N atoms resulting in different abilities to bind metal ions, are also included in the invention.

Also included are peptides which have been modified so as to optimize solubility properties or to mediate activation by a cell-associated substance. Analogs can differ from naturally occurring agents by alterations of their primary amino acid sequence. These peptides include genetic variants, both natural and induced. Induced mutants can be made by various techniques, e.g., by random mutagenesis of the encoding nucleic acids using irradiation or exposure to ethyl methanesulfonate (EMS), or by site-specific mutagenesis or other techniques of molecular biology, such as polymerase chain reaction (PCR). Also included are analogs which include residues other than naturally occurring L-amino acids, e.g., D-amino acids, non-naturally occurring or synthetic amino acids, e.g., $\beta$ or $\gamma$ amino acids, or L-amino acids with non-natural side chains using known methods. Methods for site-specific incorporation of non-natural amino acids into the protein backbone of proteins is described in Ellman et al., Science 255:197, 1992, and Noren et al., Science 244:182–188, 1989. The peptides of the invention are not limited to products of any of the specific exemplary process listed herein.

Useful mutants can be identified using the inventive screening assay, in which a combinatorial library containing a semi-random mutational cassette is screened for activity or the ability to be activated by a condition or substance.

Cell-Specific Ligands

The delivery portion or cell-specific ligand of the compound can be any ligand which binds specifically to the target cell. The invention can employ not only intact monoclonal or polyclonal antibodies, but also an immunologically-active antibody fragment, such as a Fab' or (Fab')$_2$ fragment, or a genetically engineered Fv fragment (Ladner et al., U.S. Pat. No. 4,946,788).

Delivery agents can also include other cell-specific ligands, e.g., hormones such as steroid hormones, or peptide hormones; neuroactive substances, e.g., opioid peptides; insulin; growth factors, e.g., epidermal growth factor, insulin-like growth factor, fibroblast growth factor, platelet derived growth factor, tumor necrosis factor; cytokines, e.g., an interleukin (IL), e.g., IL-2, IL-4, or IL-5; melanocyte stimulating hormone; a substance or receptor which has affinity for a particular class of cells (or viruses) e.g., cancer cells, virally infected cells, immune cells, e.g., B cells or T cells or a subset thereof, e.g., soluble fragments of CD4, which bind to the protein gp120 expressed on HIV-infected cells; or a substance with an affinity for a class of molecules, e.g., a lectin, e.g., concanavalin A, which binds a subset of glycoproteins. Adhesion molecules, e.g., molecules expressed on cells of hematopoetic origin, such as CD2, CD4, CD8 which are expressed on T cells, selecting, integrins, as well as adhesion molecules expressed on non-immmune cells, may also be used as delivery agents to direct the compound of the invention to target cells. Since some cancer cells abnormally express certain adhesion molecules, receptors for such adhesion molecules may also be used as delivery agents.

Linkage of Lytic Pore-Forming Agents to Cell-Specific Ligands

The two functional components of the compound of the invention are linked together via a covalent or non-covalent bond, or both. Non-covalent interactions can be ionic, hydrophobic, or hydrophilic, such as interactions involved in a leucine-zipper or antibody-Protein G interaction (Derrick et al., Nature 359:752, 1992).

A covalent linkage may take the form of a disulfide bond. The DNA encoding one of the components can be engineered to contain a unique cysteine codon. The second component can be derivatized with a sulfhydryl group reactive with the cysteine of the first component. Alternatively, a sulfhydryl group, either by itself or as part of a cysteine residue, can be introduced using solid phase polypeptide techniques. For example, the introduction of sulfhydryl groups into peptides is described by Hiskey (*Peptides* 3:137, 1981).

Proteins can be chemically modified by standard techniques to add a sulfhydryl group. For example, Traut's reagent (2-iminothiolane-HCl) (Pierce Chemicals, Rockford, Ill. can be used to introduce a sulfhydryl group on primary amines, such as lysine residues or N-terminal amines. A protein or peptide modified with Traut's reagent can then react with a protein or peptide which has been modified with reagents such as N-succinimidyl 3-(2-pyridyldithio) propionate (SPDP) or succinimidyl 4-(N-maleimidomethyl)cyclohexane-1-carboxylate (SMCC) (Pierce Chemicals, Rockford, Ill.

A free sulfhydryl group of an antibody may be generated using methods known to the art. For example, the antibody can be enzymatically cleaved with pepsin to yield (Fab')$_2$ fragments, which are then gently reduced with dithiothreitol (DTT) or 2-mercaptoethanol to yield free sulfhydryl-group-containing Fab' fragments. Antibody fragments, e.g., single chain Fv, can also be expressed recombinantly and genetically engineered to contain a terminal cysteine group using methods known to the art or chemically modified as described above.

Once the correct sulfhydryl groups are present on each component of the compound, the two components are purified, sulfur groups on each component are reduced; the components are mixed; and disulfide bond formation is allowed to proceed to completion at room temperature. To improve the efficiency of the coupling reaction, the cysteine residue of one of the components, e.g., cysteine-αHL, can be activated prior to addition to the reaction mixture with 5,5'-dithiobis(2-nitrobenzoic) acid (DTNB) or 2,2'-dithiopyridine, using methods known to the art. Following the reaction, the mixture is dialyzed against phosphate buffered saline to remove unconjugated molecules. Sephadex chromatography or the like is then carried out to separate the compound of the invention from its constituent parts on the basis of size.

The components of the chimera can also be joined using the polymer, monomethoxy-polyethylene glycol (mPEG), as described in Maiti et al., Int. J. Cancer Suppl. 3:17–22, 1988, herein incorporated by reference.

If the compound of the invention is produced by expression of a fused gene, a peptide bond serves as the link between the pore-forming agent and the cell-specific ligand. For example, a recombinant fusion protein of a single chain Fv fragment of an antibody and a pore-forming agent can be made according to methods known in the art (Huston et al., Meth. Enzymol. 203:46–88, 1991).

Activating Conditions or Substances

An inactive compound of the invention can be activated at the surface of the target cell by certain conditions or substances. These conditions or substances may be endogenously provided by the cell itself or exogenously provided by a source other than the target cell. Physical, chemical or biochemical conditions can activate lytic activity. Such conditions may activate the compound of the invention by inducing a conformational change in one or both of the components of the chimera. Any physical condition, such as a heat or light at the surface of the target cell can be used to activate the compound of the invention. Since temperature increases and changes in pH have been associated with certain tumor cells compared to normal cells, a heat-sensitive or pH-sensitive moiety can be used to confer the ability to be activated by such cells. In another example, a compound of the invention which is activatable by light can be particularly useful for the purging of unwanted leukemic cells from blood by transiently exposing blood to light via a UV-emitting extracorporeal device. Accessible tumors such as skin cancers can also be treated in this manner, and relatively inaccessible tumors, such as lung cancers, can be reached using light emissions from fiber optic devices.

Chemical conditions, such as pH, reducing potential or the presence of metal ions, may also serve as activators. For example, the compound of the invention can be modified to contain a protecting group which is altered or removed by exposure to a chemical condition at the surface of the target cell, thus resulting in the activation of lytic activity. Since metastatic cancer cells have been shown to secrete matrix metalloproteinases (Liotta et al., Cell 64:327–336, 1991), a metalloproteinase recognition site that has been incorporated into the compound of the invention can be acted upon by the enzyme at the surface of a tumor cell, resulting in the activation of pore-forming function. In another example, metal ions or chelating agents, e.g., ethylenediaminetetraacetic acid (EDTA), may be infused into the animal systemically or directly into the site of the target cell to activate or deactivate lytic function.

Lytic pore-forming activity can also be activated biochemically. Any substance secreted by or associated with an unwanted cell, such as an enzyme, e.g., protease, esterase, glycosidase, ectokinase, phosphatase, capable of acting upon the compound of the invention at the surface of the target cell, resulting in the activation of pore-forming function can be used.

Therapeutic Administration

The compound of the invention can be administered to an animal, e.g., a human, suffering from a medical disorder, e.g., cancer, or other conditions characterized by the presence of a class of unwanted cells. For example, therapeutic destruction of CD8-bearing T cells in HIV-infected patients may be efficacious in restoring a proper ratio of CD4 to CD8 cells in such patients (Rennie, Sci. Amer. 5/93:24—24).

The amount of compound administered will vary with the type of disease, extensiveness of the disease, and size of species of the animal suffering from the disease. Generally, amounts will be in the range of those used for other cytotoxic agents used in the treatment of cancer, although in certain instances lower amounts will be needed because of the increased specificity of the compound. The compound of the invention may be used in combination therapy in which the compound of the invention is administered either simultaneously or sequentially with a therapeutic agent which is not easily internalized by the target cell, such as cytotoxic chemotherapeutic agents, described above. For example, an oligomeric anti-sense DNA can be used to eliminate or down-regulate the expression of genes necessary for cell survival. Permeabilization of target cells by the compound of the invention can also facilitate the entry of ribozymes into the target cell, which can kill the cell by disrupting protein synthesis.

Generally, the compound of the invention will be administered by intravenous infusion, although it may also be administered subcutaneously or injected directly into site at which unwanted cells are to be destroyed, e.g. a tumor site. The compound can also be aspirated to the tumor site via bronchial passages to treat cancers of the lung. Topical administration, e.g., in a cream formulation, to kill primary cancer cells such as skin cancers, can also be used and systemic administration via injections or implants is favored to kill metastatic cells. The compound of the invention can be combined with any non-toxic, pharmaceutically-acceptable carrier substance for administration to animals or humans.

The mutant activatable pore-forming agent of the invention which is not linked to a cell-specific ligand can be administered as described above. In this case, the specificity of the pore-forming agent is determined by the activating condition or substance, at the surface of the target cell. For example, a tumor-specific protease produced by a metastatic cancer cell can activate the lytic function of the inactive pore-forming agent, thus leading to the destruction of the cancer cell but not the destruction of a cell which does not produce the activating substance.

EXAMPLE 1:

PROTEASE-ACTIVATED αHL

We will now describe a genetically-engineered lytic pore-forming agent which can be specifically activated by a protease.

αHL mutants

Mutants of αHL were generated from the plasmid pT7-NPH8S, which encodes the wild-type sequence of αHL as secreted by *Staphylococcus aureus*. pT7-NPH8S was made from pT7-NPH8 (Walker et al, J. Biol. Chem. 268:21782, 1992, ) by using oligonucleotide-directed mutagenesis to correct the mutation, Ser-217→Asn, that occurred during an earlier PCR. The codon Lys-8 in pT7-NPH8S was then changed to Ala by oligonucleotide-directed mutagenesis to eliminate an unwanted protease recognition site.

Truncated αHL genes were generated from the K8A gene by PCR using procedures described in Walker et al., supra. To obtain overlap mutant K8A,K131R(1–172●132–293), K8A,K131R was made from K8A by oligonucleotide-directed mutagenesis and then K8A,K131R1–172) was generated from K8A,K131R by PCR.

Coupled IVTT

Full length recombinant αHL(Walker et al., J. Biol. Chem. 267:10902–10909, 1992 ), truncated recombinant αHL polypeptides (Walker et al., J. Biol. Chem. 267:21782–21786, 1992 ), and recombinant two-chain complementary αHL polypeptides (Walker et al., J. Biol. Chem. 268:5285–5292) were then produced by IVTT according to methods known in the art by using anE. coli S30 extract (Promega No. L4500). The mix was supplemented with T7 RNA polymerase (NEB No. 251L, added at 2000 U/mL) and rifampicin (20 μg/mL) and ($^{35}$S) methionine. For hemolysis assays, the final methionine concentration in the IVTT mix was 0.5 mM (0.8 Ci/mmol) to ensure the synthesis of mutant polypeptides at concentrations in the range 10–50 μg/mL. Synthesis was carried out for 60 min at 37° C. The integrity of the translation products and their relative concentrations were evaluated by SDS-PAGE and autoradiography.

Expression of recombinant proteins by bacteria, yeast, or other eucaryotic cells, using methods well-known in the art, is preferable for large-scale production of the compound.

Hemolysis assay

To assay hemolysis in microtiter wells, IVTT extracts, untreated or treated with endo C were diluted 4-fold in well 1 (based on the mix volume before additions of protease etc.) in 20 mM K-phosphate, 150 mM NaCl, pH 7.4 containing 1 mg/mL bovine serum albumin (K-PBSA), and then subjected to two-fold serial dilutions in K-PBSA. Washed rabbit erythrocytes were then added to 0.5% and the plate was incubated at 20° C. In the spectrophotometric assay, hemolysis was monitored at room temperature (25° C.) by the decrease in light scattered at 600 nm after the addition of IVTT mix (10 μL) to rabbit erythrocytes diluted to 0.025% in K-PBSA (500 μL).

Proteolysis

Overlap mutants were activated by adding endo C (Promega No. V544A: 1 μg/1 μl in 25 mM NaH$_2$PO$_4$, 1 mM EDTA, pH 7.5) to the IVTT mix (10 μl). After 10 min. at 30° C., the protease was inactivated with TLCK (1 mM). For clostripain treatment, IVTT mix (10 μL) was incubated for 15 min at 30° C. with enzyme (Sigma No. C-7403 0.1 μg) that had been activated in 50 mM Tris-HCl containing 2.5 mM DTT. Clostripain can also be inactivated with 1 mM TLCK.

Samples for electrophoresis were dissolved in 1X loading buffer, heated at 95° C. for 2 min., and subjected to electrophoresis in a 12% SDS-polyacrylamide gel (U.K. Laemmli, Nature 227:680, 1970). Radiolabelled markers (Gibco BRL) were ($^{14}$C)methylated proteins; myosin heavy chain ($M_r$=200,000); phosphorylase b ($M_r$=97,400); bovine serum albumin ($M_r$=68,000); ovalbumin ($M_r$=43,000); carbonic anhydrase ($M_r$=29,000); β-lactoglobulin ($M_r$=18,400); lysozyme ($M_r$=14,300).

Hexamer Formation

IVTT was carried out in the presence of ($^{35}$S)methionine (1200 Ci/mmol) and the reaction was stopped by the addition chloramphenicol (100 μM) and unlabelled methionine (5 mM), which prevent the incorporation of $^{35}$S into rabbit erythrocyte membrane proteins. IVTT mix (5 μL), untreated or treated with endo C (1 μg), was incubated with 10% rabbit erythrocytes (50 μL) for 60 min at 20° C. in K-PBSA. The cells or membranes were recovered by centrifugation, dissolved in 30 μL 1X loading buffer (U.K. Laemmli, Nature 227:680, 1970), warmed at 45° C. for 5 min. and subjected to electrophoresis in a 12% SDS-polyacrylamide gel.

Characterization of αHL mutants

Staphylococcal α-hemolysin, a lytic pore-forming toxin, has been remodeled yielding inactive molecules that can be activated by Lys/Arg-directed proteases, which inactivate the wild-type protein. Wild type αHL polypeptides with nicks near the midpoint of the central glycine-rich loop (Walker et al., supra) are held together by a domain-domain interaction and are hemolytically active. By contrast, mutant αHL proteins comprising two αHL truncation mutants that overlap in the central loop (overlap mutants) have no or greatly reduced pore-forming activity. Overlap mutants have now been designed that are activated when redundant amino acids in the loop are removed by proteases.

Trypsin cleaves βHL after Lys-131 near the midpoint of the central loop (Walker et al., supra). However, wild-type αHL is inactivated by trypsin because of cleavage at a second site after Lys-8. The mutant αlHL, K8A, in which Lys-8was replaced with alanine, has the same hemolytic activity as the wild-type αHL, but is resistant to trypsin and related proteases.

Several overlap mutants were then generated from K8A by in vitro cotranslation of transcripts from two plasmids, each containing a truncated αHL gene. In all cases, the trypsin cleavage yielded the fragment combination, 1–131 and 132–293, which has strong hemolytic activity. Untreated overlap mutants were weakly active or inactive as determined by hemolysis assays and they were activated by the lysine-and arginine-directed trypsin or the lysine-directed endo C (FIGS. 1a–1c and FIGS. 2a–2d).

Mechanism of proteolytic activation

Figure 1A:
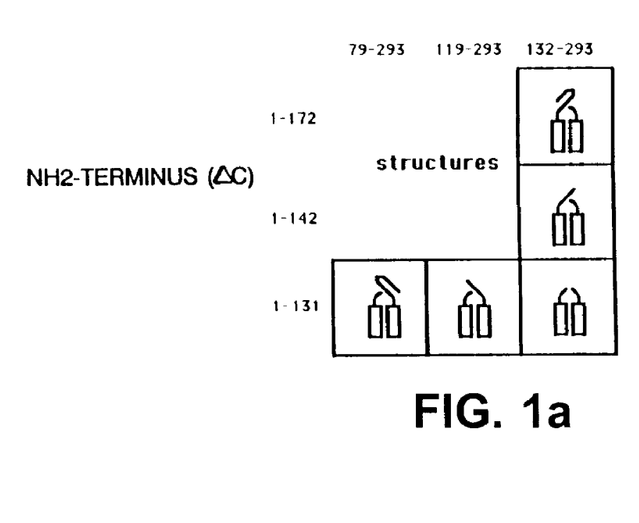
Figure 1B:
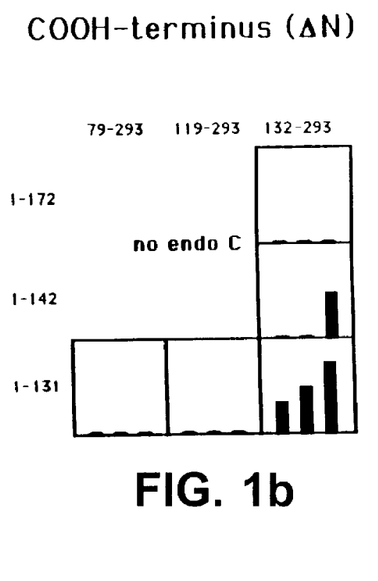
Figure 1C:
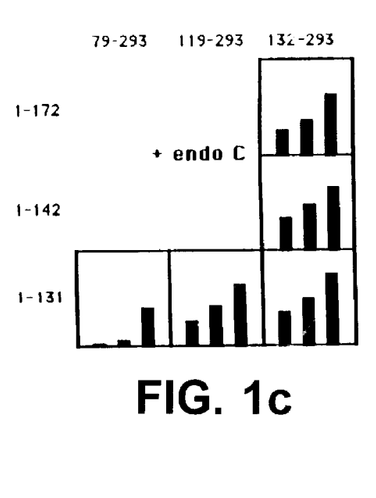
Figure 2A:
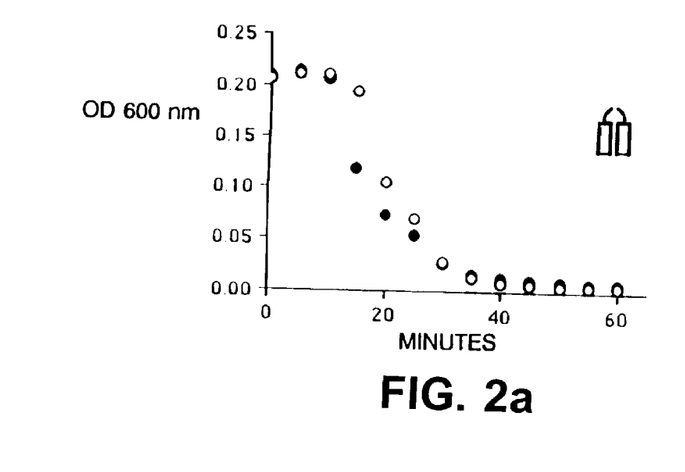
Figure 2B:
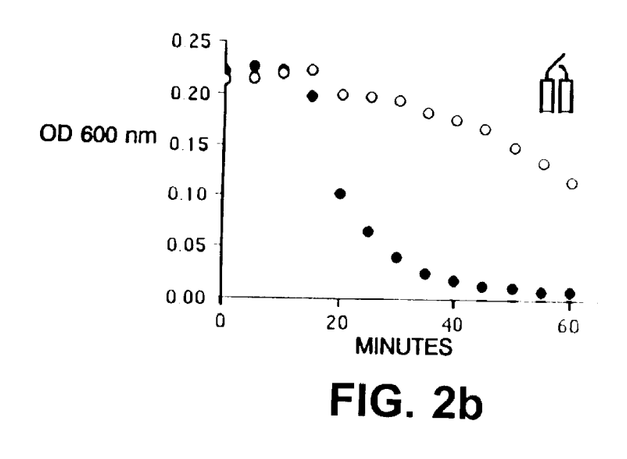
Figure 2C:
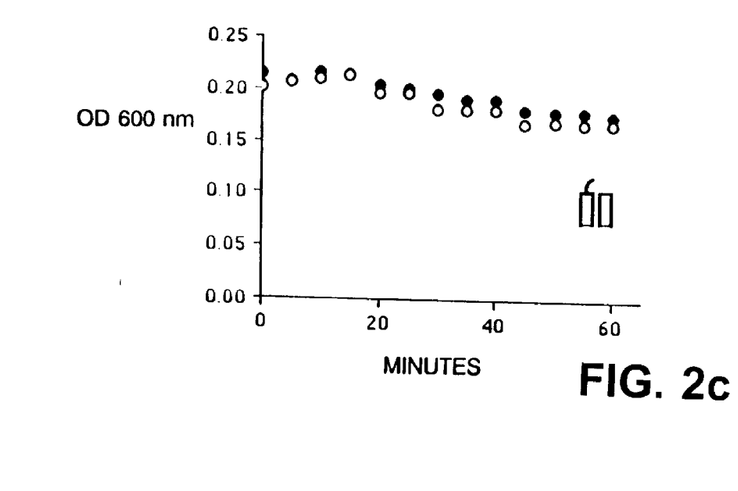
Figure 2D:
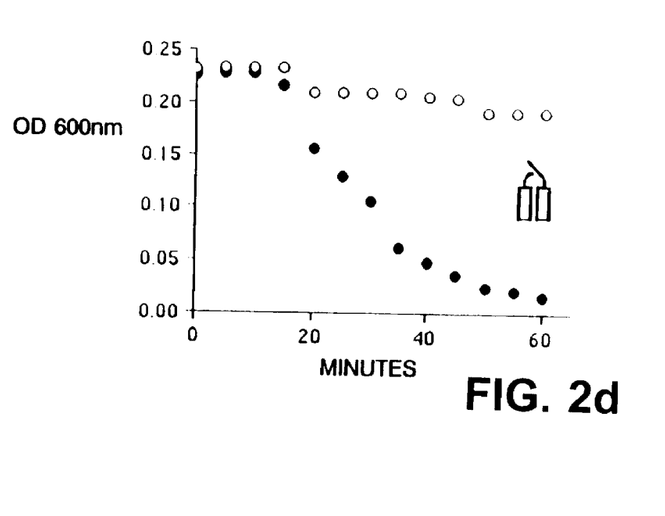
Figure 3A:
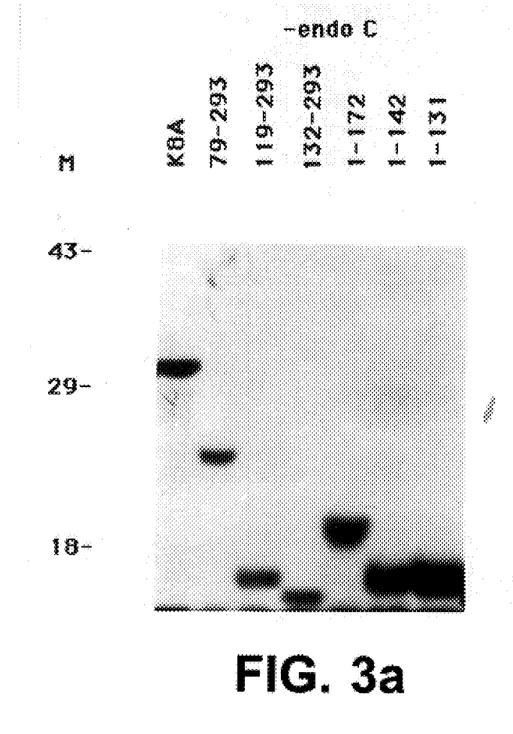
FIG. 3a shows untreated individual chains and FIG. 3b shows individual chains treated with endo C (1 μg added to 6 μL IVTT mix).
Figure 3B:
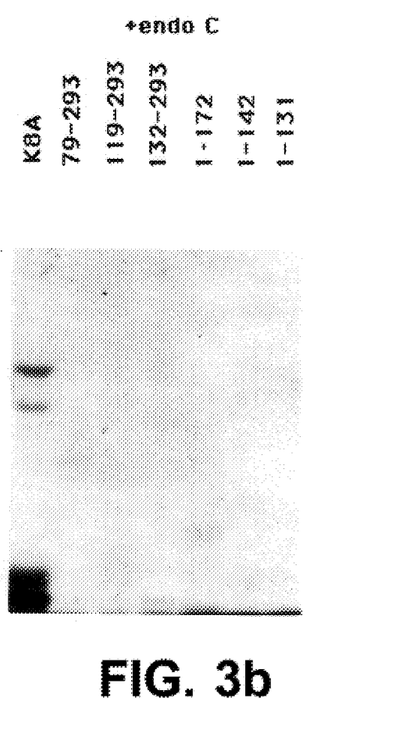
Figure 4A:
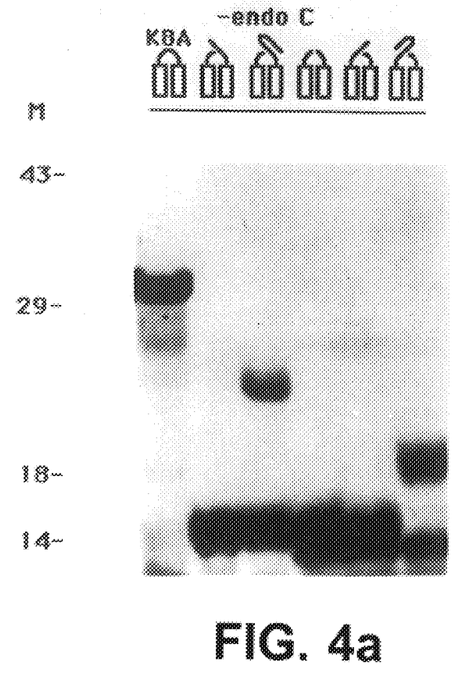
FIG. 4a shows untreated two-chain mutants and FIG. 4b shows two-chain mutants treated with endo C (1 μg added to 12 μL IVTT mix). The two-chain mutants are converted to fragments that co-migrate with polypeptides 1–131 and 132–293. These fragments are resistant to further breakdown. In the cases of mutants with forward overlaps, a full-length αHL polypeptide is also generated.
Figure 4B:
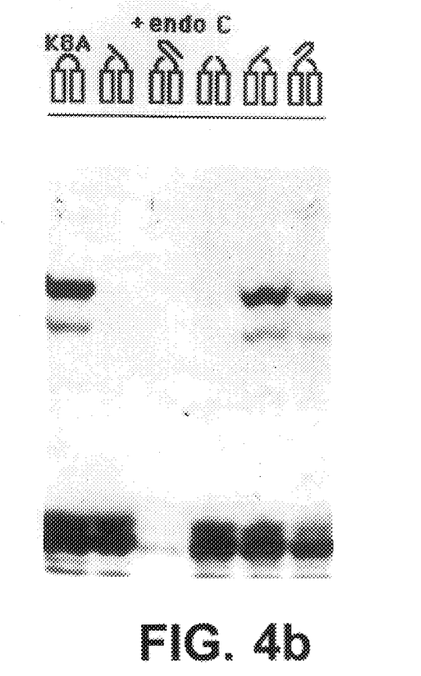
Figure 5:
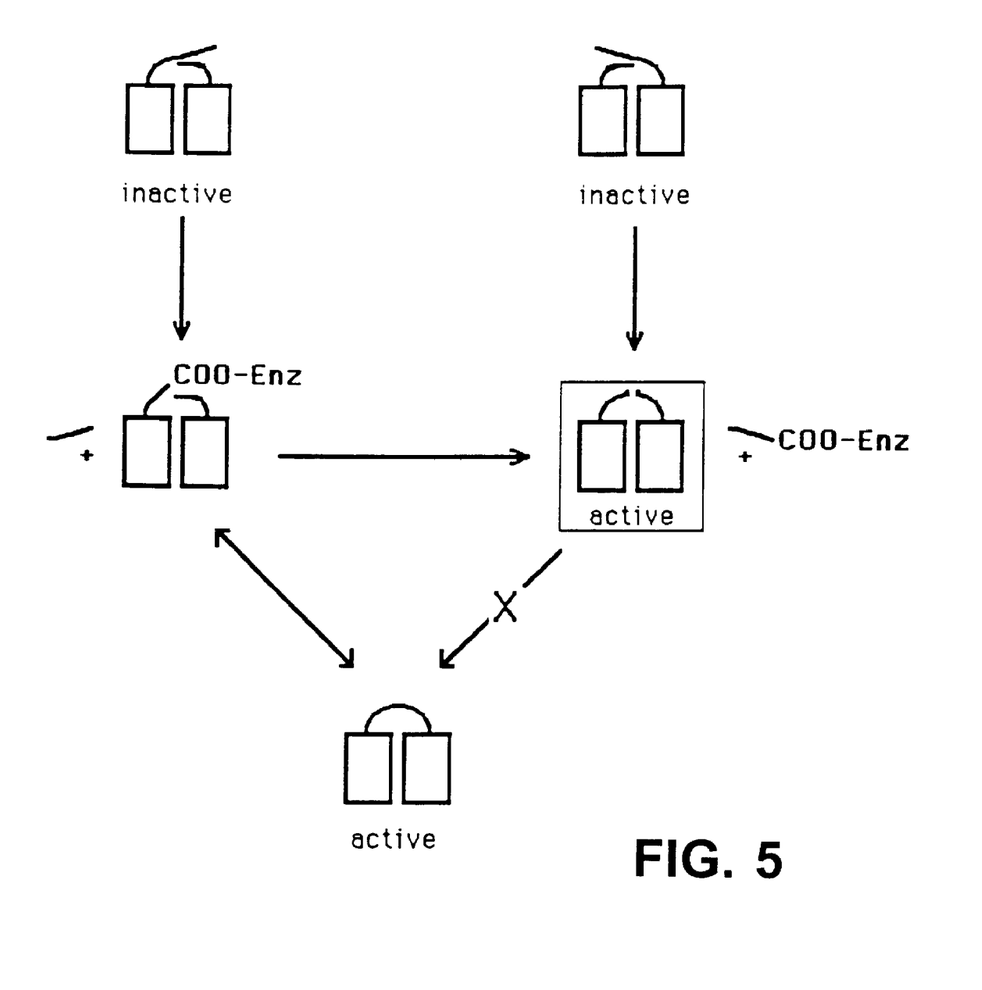
FIG. 5 is a schematic interpretation of the proteolysis data. The final state of both forward and reverse overlap mutants is boxed.
Figure 6A:
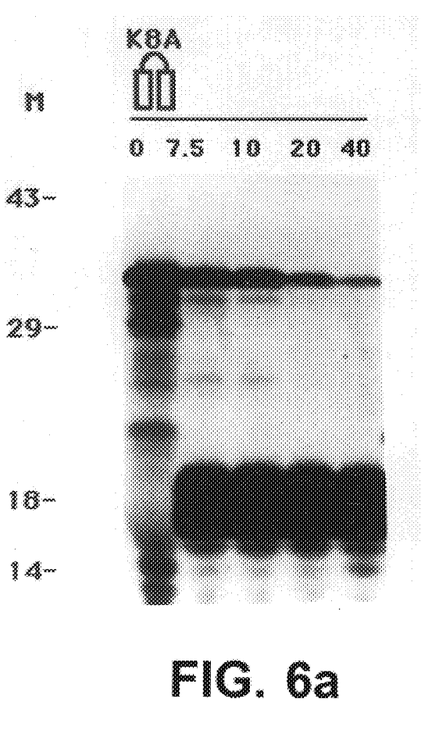
FIGS. 6a–6b are photographs of a SDS-PAGE gel showing the time course of proteolysis of the overlap mutant K8A (1–172)●(132–293) with endo C (right). Proteolysis results in the formation of two chains, 1–131 (open arrow) and 132–293 (closed arrow) without further degradation. IVTT mix (12.5 μL), produced using ($^{35}$S)methionine at 1200 Ci/mmol, was treated with endo C (1.0 μg) at 30° C. Aliquots were removed after designated times and treated with 1 mM Nα-ptosyl-L-lysine chloromethyl ketone (TLCK). Proteolysis of single-chain K8A was performed as a control (FIG. 6a).
Figure 6B:
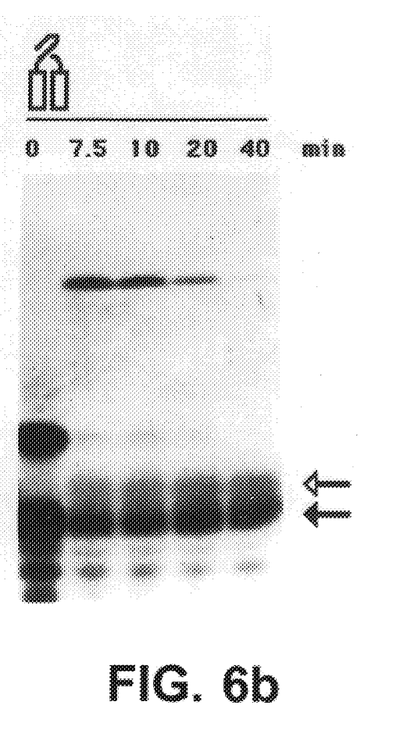

Overlap mutants and single polypeptide chains from which they were derived were cleaved with endo C. The single chains, encompassing large N-terminal or C-terminal fragments of αHL were rapidly digested into small peptides (FIGS. 3a–3b). By contrast, when incorporated into overlap mutants, the same chains were converted to the fragments 1–131 and 132–293, but were otherwise resistant to the protease (FIGS. 4a–4b). The full-length polypeptide generated from forward overlap mutants (1–142●132–293 and 1–172●132–293: additional amino acids on the N-terminal polypeptide) can contain a normal peptide bond at the fusion site, because it is cleaved at the 131–132 bond upon further exposure to endo C (FIG. 5, FIGS. 6a–6b).

Selective activation

Figure 7A:
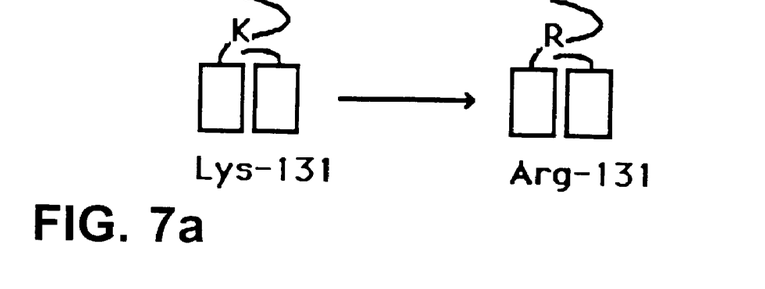
Figure 7B:
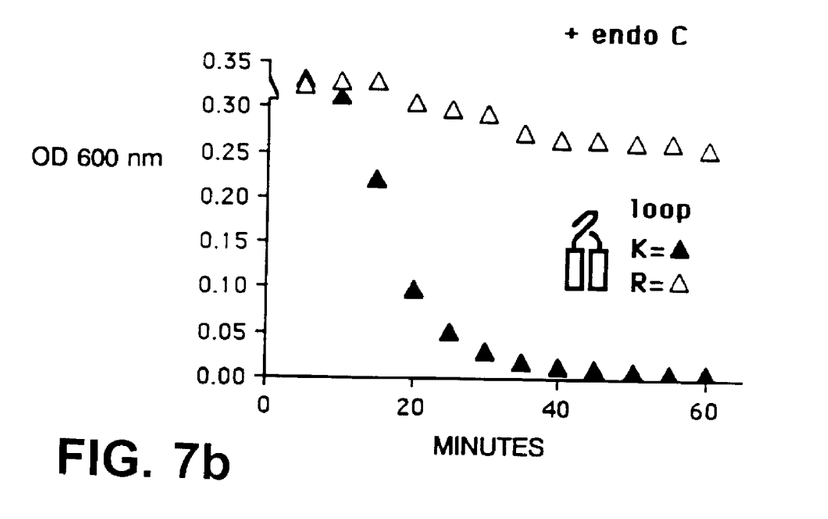
FIG. 7b shows the results after endo C activation and FIG. 7c panel shows the results after clostripain activation.
Figure 7C:
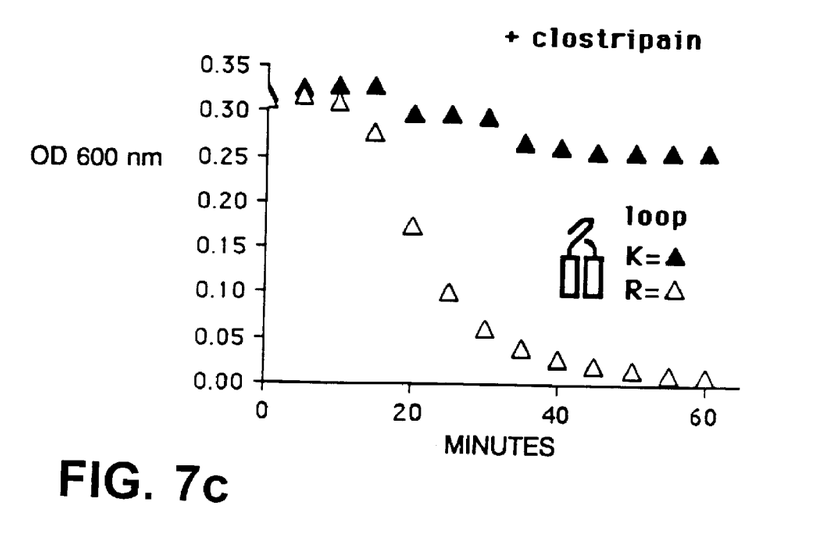

The requirement for protease specificity was tested by altering the recognition sequence in the central loop. Two overlap mutants, 1–142●132–293 and 1–172●132–293, were produced from the double point mutant K8A,K131R, and compared with the same overlap mutants generated from K8A. The Lys-131-containing mutants were selectively activated by the lysine-directed endo C and the Arg-131 mutants selectively activated by the arginine-directed clostripain (FIGS. 7a–7c).

EXAMPLE 2:

METAL-RESPONSIVE LYTIC PORE-FORMING AGENTS

We will now describe a mutant αHL which is responsive to metal ions.

Metal-ion sensitivity

Figure 8:
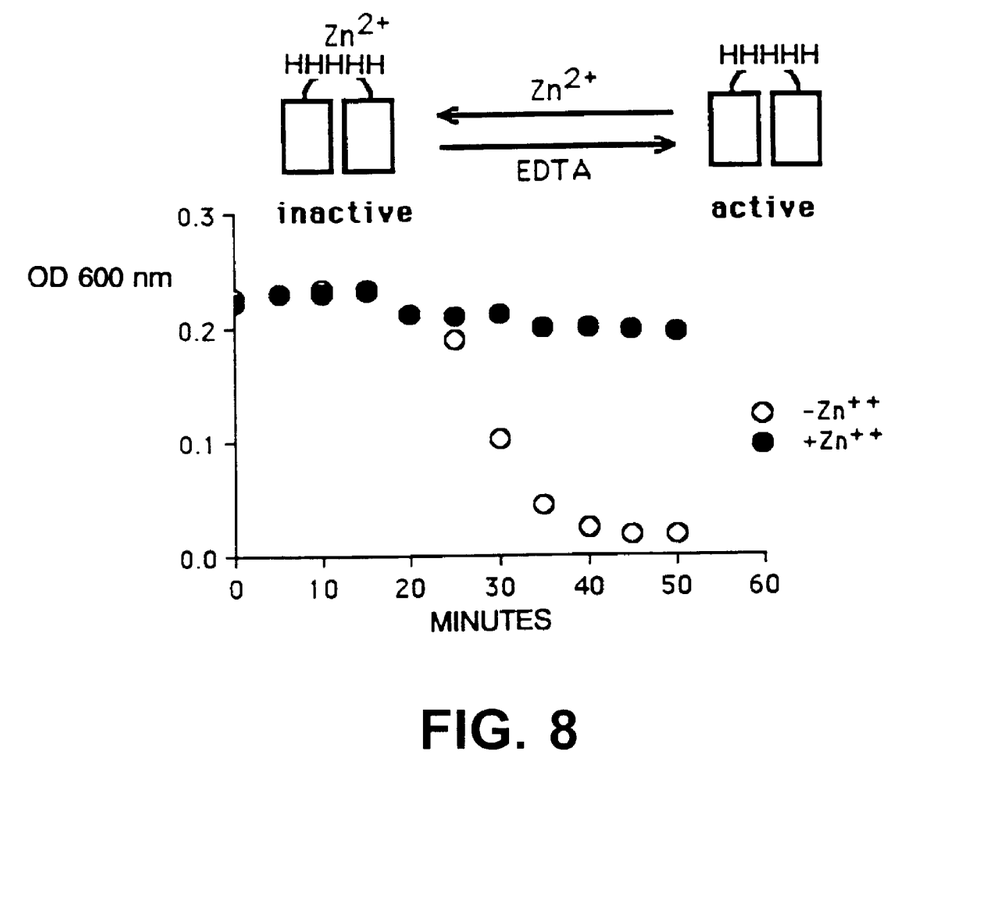
FIG. 8 is a graph showing the results of a spectrophotometric assay for hemolysis by αHL-H5m in the presence or absence of 10 μM $ZnSO_4$. The decrease in light scattered at 600 nm was monitored after the addition of purified αHL-H5m (0.4 mg/ml, 1.0 μL) to 0.025% rabbit erythrocytes (500 μL). The assay was carried out at room temperature with rabbit erythrocytes diluted to 0.025% in 20 mM K-phosphate, 150 mM NaCl, pH 7.4.
Figure 9:
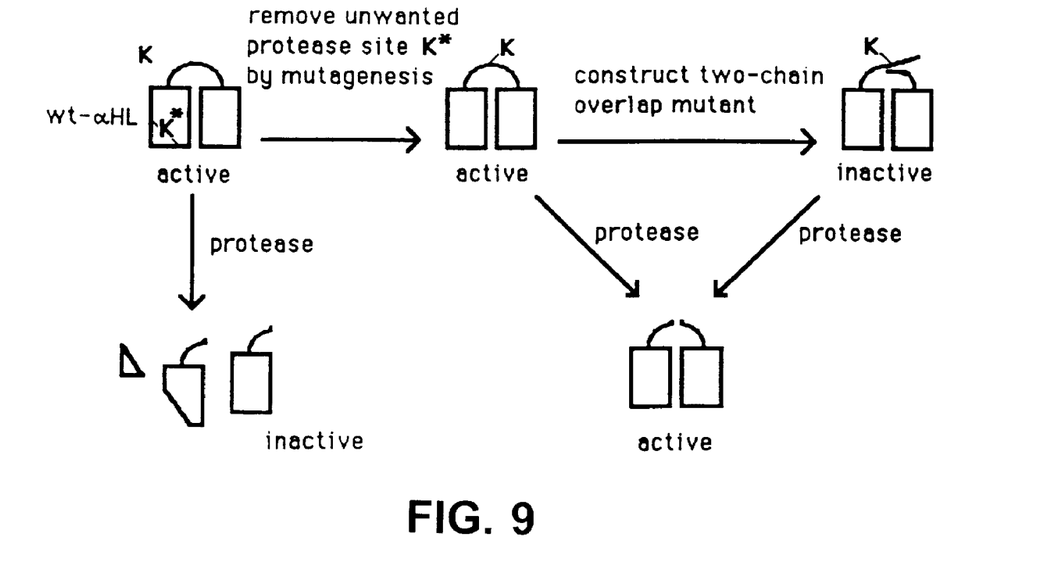
FIG. 9 is a diagram showing construction of a protease-activated mutant αHL from a protease-sensitive wild-type αHL.
Figure 10:
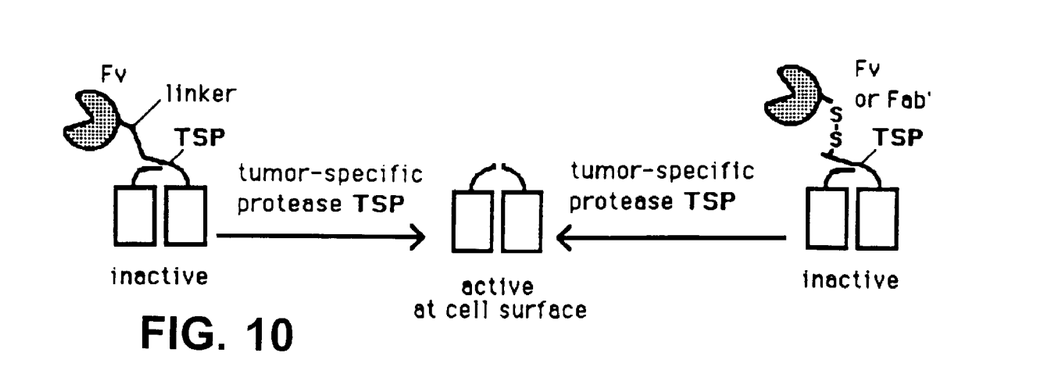
FIG. 10 is a diagram showing the structure of a chimeric compound of the invention in an inactive form and its structure after conversion to an active form by a tumor-specific protease.

A metal-sensitive αHL was produced by replacing residues 130–134 in the glycine-rich loop with five consecutive histidines. The hemolytic activity of this mutant, designated αHL-H5m, can be inactivated by $Zn^{2+}$(10 αM) and reactivated with EDTA (2 mM), as shown in FIG. 8. In contrast, the wild type αHL is unaffected by $Zn^{2+}$under the same conditions. Such metal-responsive agents can be inactivated by metals prior to administration to patients and activated in the patient by the administration of low levels of metal chelators, such as EDTA.

Lytic pore-forming agents which are activated by the presence of metal ions can also be used. The modification and introduction of other metal-binding amino acids, such as cysteine and non-natural amino acids discussed above, can also be introduced into αHL to confer metal-ion sensitivity. Mutants which are activated or inactivated by other metal ions, such as divalent Group IIB and transition metals (Co, Ni, or Cu) can be identified using the screening assay of the invention, described below.

EXAMPLE 3:

αHL-AB CONSTRUCTS

We will now describe a genetically-engineered inactive mutant of αHL linked to a target cell-specific antibody.

Construction of Ab-αHL conjugates

Any protease, which is specifically associated with a particular cell type, can be employed as an activator of inactive compounds of the invention, e.g., plasminogen activator, specifically urokinase-type plasminogen activator (uPA), which has been specifically associated with the metastatic phenotype of cancer cells (Liotta et al. Cell 64:327–336, 1991). The recognition sequence of plasminogen activator, Gly-Arg, or the same sequence preceded by a negatively charged amino acid, the recognition sequence for uPA, can be incorporated into the compound of the invention for the purpose of specific activation of the pore-forming agent. Similarly, the autocatalytic cleavage site for human collagenase IV (CIV) (Stetler-Stevenson et al., J. Biol. Chem. 264:1353–1356, 1989, herein incorporated by reference), can also be incorporated into the compound. These recognition sites can also serve as the basis for the semi-random combinatorial mutagenic cassette used in the generation of novel lytic pore-forming agents, described below.

Mutant two-chain αHL can be constructed as shown in FIG. 9. In the construct shown, the protease site for trypsin has been added. Since murine B16 melanoma cells have been shown to secrete plasminogen activator and collagenase IV (Reich et al. *Res.* 48:3307–3312, 1988; Wang et al., *Cancer Res.* 40:288–292, 1980), the protease cleavage sites for plasminogen activator and collagenase IV (gelatinase/MMP2) (Stack et al. *Arch. Biochem. Biophys.* 287:240–249, 1991; Stack et al. *J. Biol. Chem.* 264:4277–4281, 1989; Harrison et al. *Anal. Biochem.* 180:110–113, 1989) can also be added for specific activation by this cell type. Linker regions can be glycine- and serine-rich peptides.

A reduced Fab fragment or an Fv fragment with an engineered cysteine can also be linked to an activated single-cysteine, two-chain mutant of αHL, as shown in FIG. 10. DNA encoding Fv fragments can be produced by RT-PCR of RNA extracted from antibody-producing hybridoma cells, such as those producing anti-dinitrophenol (DNP) or anti-B16 antibody (Chaudhary et al. *Acad. Sci. USA* 87:1066–1070, 1990). For in vitro screening purposes of chimeric compounds, the gene fusion approach is favored because sufficient two-chain compound can be obtained by IVTT. The two-chain construct can be expressed in bacteria using two different plasmids, a single plasmid with dual-promoters, or a single plasmid with a bicistronic operon. However, production of each component separately, followed by the joining of the antibody or other delivery agent, using chemical conjugation methodology described above, is favored for large-scale production.

Testing of conjugates in vitro (i) Activation by trypsin: An overlap mutant of αHL which is activated by trypsin is shown in FIG. 9. Such mutants and chimeric compounds containing such mutants can be activated in vitro by treatment with the protease, trypsin (trypsin site denoted by: K), inhibiting the protease, and assaying activation by hemolytic titer.

(ii) Activation by tumor proteases: B16-F10 melanoma cells (B16) (ATCC Accession No. CRL6475) can also be used as target cells. These highly metastatic cells secrete plasminogen activator and collagenase IV (Reich et al., supra; Wang et al., supra). Target cells can be lysed by activating antibody-PA-αHL (PA denotes the recognition sequence of the enzyme, plasminogen activator) and antibody-CIV-αHL (CIV denotes the recognition sequence of the enzyme, collagenase IV) in vitro, by using, as appropriate, plasminogen activator, collagenase IV and secretions from cells producing such enzymes.

Activation on the surface of target cells (i) Target cells; DNP-human erythrocytes: Active wild type αHL efficiently lyses rabbit erythrocytes, which bear αHL receptors, but not human erythrocytes and other cells which do not bear receptors for αHL. The surfaces of human erythrocytes, which are resistant to αHL-mediated lysis, must first be modified with dinitrophenol fluoride (DNP-F) to make them susceptible to lysis. The derivatized cells can then be treated with anti-DNP-K-αHL, washed, and then incubated with trypsin. In this example, the anti-DNP antibody serves to direct the compound to the derivatized target cells, resulting in increased local concentration of αHL polypeptides on the surface of cells which triggers the assembly of pores.

(ii) DNP-B16 melanoma cells: B16 melanoma cells can also be modified with DNP-F and then treated with anti-DNP-PA-αHL or anti-DNP-CIV-αHL. In this case, target cell viability can be assayed in vitro over 3 days by standard assays including trypan blue exclusion, $^{51}$Cr release, [$^{35}$S] methionine uptake (protein synthesis) and [$^{3}$H]thymidine uptake (DNA replication) as an indication of the ability of the compound to permeabilize the target cells.

B16-specific antibody linked to αHL, e.g., anti-B16-PA-αHL or anti-B16-CIV-αHL, can be used to direct the compounds of the invention to the surface of B16 melanoma cells which have not been treated with DNP. Cell viability after incubation with the compound of the invention can be assayed as described above.

Selective permeabilization of target cells

Certain nucleated cells are often able to repair damage to the plasma membrane and might not be as readily disrupted as erythrocytes, however this limited permeabilization induced by the compound of the invention can be useful for the administration of therapeutic agents, which are normally poorly internalized by cells. For example, methotrexate-γ-aspartate, an analog of the chemotherapeutic drug methotrexate, is normally non-toxic because of its inability to be internalized by cells but highly cytotoxic when it gains entry to the cytoplasm of a cell. Selective permeabilization of target cells can be used to facilitate the entry of this drug into tumor cells. Such a treatment strategy could minimize the side effects of chemotherapy, since the drug could only be taken up by permeabilized cells and would thus remain non-toxic to intact cells.

In another example, selective permeabilization of target cells can mediate a toxic influx of $Ca^{2+}$ into cells. Normally, intracellular $Ca^{2+}$ is maintained at a very low concentration (0.05–0.2 μM). Extracellular $Ca^{2+}$ levels are about four orders of magnitude greater (1.3 mM). Prolonged increases in intracellular free $Ca^{2+}$ can result in cell death and is thought to be the underlying mechanism of neuronal death in victims of stroke and neurodegenerative diseases (Randall et al., J. Neurosci. 12:1882–1895, 1992). Compounds of the invention can be used to direct $Ca^{2+}$ mediated killing to specific target cells by permeabilizing the target cells and permitting the influx of extracellular $Ca^{2+}$. Selective permeabilization of target cells can also be useful to facilitate the uptake of other cytotoxic agents, such as antisense oligonucleotide sequences or ribozymes.

EXAMPLE 4:

SCREENS FOR ACTIVATABLE PORE-FORMING LYTIC AGENTS

A novel screening technique to identify lytic pore-forming agents which can be activated by cell-associated substances or conditions will now be described.

Figure 11:
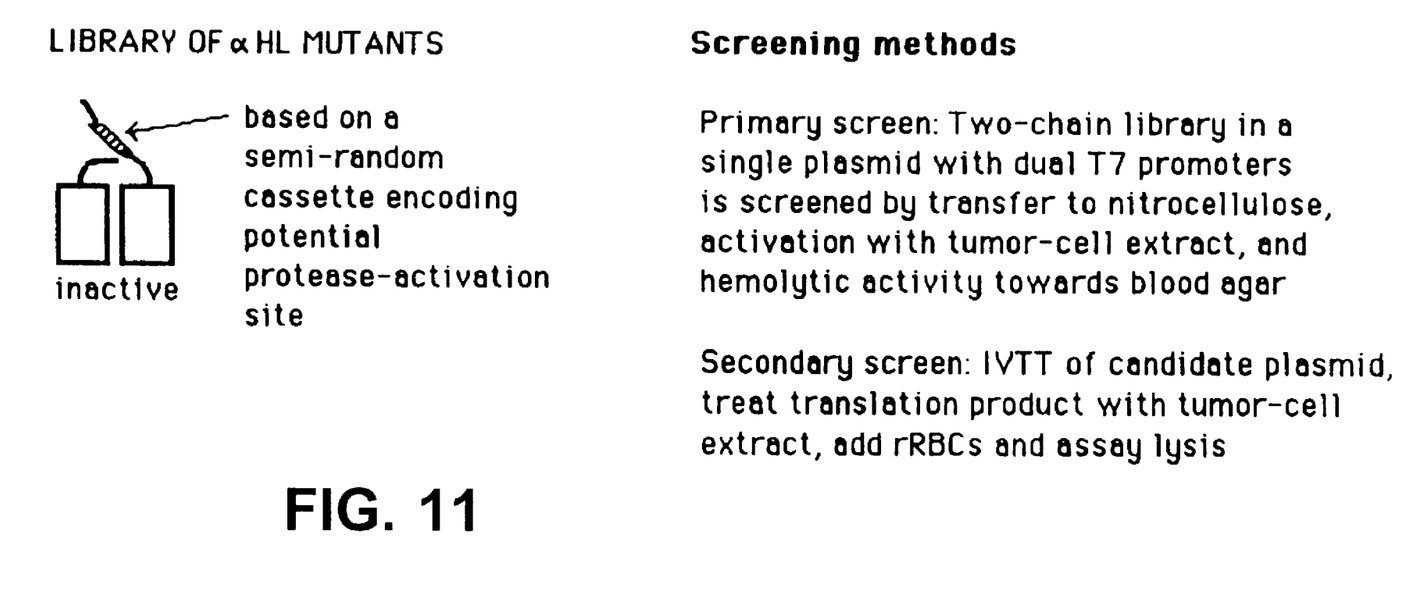
FIG. 11 is a diagram showing the method of screening a combinatorial library for pore forming agents which are activated by cell-specific substances.

Protease site selection by combinatorial mutagenesis:

A novel screening technique, based on combinatorial mutagenesis, has been devised for determining the peptide sequence specificity of proteases secreted by tumors and, at the same time, obtaining lytic pore-forming agents that are more rapidly and selectively activated by these proteases. These mutants can be then be used as cytotoxic agents against the same cells (FIG. 11). For example, mutant αHLs can be screened from combinatorial libraries on the basis of their ability to be activated by target cell extracts to lyse rabbit erythrocytes. A mutagenic cassette, containing random nucleic acid sequences generated by methods well known in the art, can be incorporated into the plasmid encoding the pore-forming agent. Since the aspects of the specificity of certain relevant proteases is known, the engineered protease sites encoded by the mutagenic cassette can be based on these sequences and need not be completely random.

For example, candidate clones from a combinatorial plasmid library can be plated on replicate nitrocellulose filters. The bacterial colonies on the filters are then lysed and recombinant proteins allowed to bind to the filters. One replicate filter is contacted with a cell extract of a target cell and as a control, a duplicate filter remains untreated. Both filters are exposed to blood agar plates and scored for the appearance of hemolytic plaques. Alternatively, the filters may be simultaneously contacted with cell extract and blood agar. The appearance of hemolysis on the plates containing filters which had been contacted with cell extract and the corresponding absence of hemolysis on plates containing untreated filters indicates that the candidate clone produces a hemolytic molecule that is activatable by a substance in the cell extract of the target cell. The screening process can be iterative in that a newly identified mutant can undergo further rounds of mutagenesis and screening as described above to identify mutants with improved activation capabilities.

Following the identification of such a colony, the plasmid can then be purified from the bacterial cells according to methods well-known in the art and analyzed to determine the DNA sequence of the mutagenic cassette. The candidate pore-forming compound can be expressed by IVTT and subjected to further analysis. The ability of the candidate pore-forming compound to be activated by the target cell can further be confirmed by incubating the translation product in the presence and absence of target cell extract, adding target cells, and assaying target cell lysis.

Selection of metal-sensitive mutants

A similar strategy using the screening assay of the invention can also be used to identify mutants with metal binding capabilities. As above, the screen can be based on a semi-random mutagenic cassette since complexity will be limited by using Cys or His codon-based oligonucleotides. As above, protein from bacterial colonies expressing αHL can be transferred to nitrocellulose filters in the presence and absence of metal ions. The duplicate filters are then placed in contact with blood agar plates and the blood agar plates scored for the appearance of hemolysis. The ability of metal ions to block or activate hemolysis can thus be evaluated.

Other embodiments are within the following claims.

What is claimed is:

1. A chimeric compound comprising an antibody or antigen binding fragment thereof linked to a mutant staphylococcal α-toxin (αHL) molecule, the pore-forming activity of which is inactive until activated by a condition or substance at the surface of said cell, wherein said mutant αHL molecule is αHL-K8A.

2. A chimeric compound comprising an antibody or antigen binding fragment thereof linked to a mutant staphylococcal α-toxin (αHL) molecule, the pore-forming activity of which is inactive until activated by a condition or substance at the surface of said cell, wherein said mutant αHL molecule is αHL-H5m.

3. A chimeric compound comprising an antibody or antigen binding fragment thereof linked to a mutant staphylococcal α-toxin (αHL) molecule, the pore-forming activity of which is inactive until activated by a condition or substance at the surface of said cell, wherein said mutant αHL molecule is αHL(1–142●132–293) and wherein mutant αHL molecule has lyine of arginine at amino acid position 131.

4. A chimeric compound comprising an antibody or antigen binding fragment thereof linked to a mutant staphylococcal α-toxin (αHL) molecule, the pore-forming activity of which is inactive until activated by a condition or substance at the surface of said cell, wherein said mutant αHL molecule is αHL(1–172●132–293) and wherein said mutant αHL molecule has lysine or arginine at amino acid position 131.

* * * * *